United States Patent [19]

Clark et al.

[11] Patent Number: 5,981,621
[45] Date of Patent: *Nov. 9, 1999

[54] MONOMERIC COMPOSITIONS EFFECTIVE AS WOUND CLOSURE DEVICES

[75] Inventors: Jeffrey G. Clark; Jeffrey C. Leung, both of Raleigh, N.C.

[73] Assignee: Closure Medical Corporation, Raleigh, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/609,921

[22] Filed: Feb. 29, 1996

[51] Int. Cl.⁶ ..................................................... A61L 25/00
[52] U.S. Cl. ........................ 523/118; 424/78.06; 424/423
[58] Field of Search .......................... 424/78.06; 523/118

[56] References Cited

U.S. PATENT DOCUMENTS

| | | |
|---|---|---|
| 2,721,858 | 10/1955 | Joyner et al. . |
| 2,765,332 | 10/1956 | Coover, Jr. et al. . |
| 2,784,127 | 3/1957 | Joyner et al. . |
| 2,784,215 | 3/1957 | Joyner et al. . |
| 2,794,788 | 6/1957 | Coover, Jr. et al. . |
| 3,354,128 | 11/1967 | Wicker et al. . |
| 3,527,841 | 9/1970 | Wicker et al. . |
| 3,554,990 | 1/1971 | Quinn et al. . |
| 3,559,652 | 2/1971 | Banitt et al. . |
| 3,591,676 | 7/1971 | Hawkins et al. . |
| 3,667,472 | 6/1972 | Halpern . |
| 3,699,127 | 10/1972 | O'Sullivan et al. . |
| 3,722,599 | 3/1973 | Robertson et al. . |
| 3,759,264 | 9/1973 | Coover, Jr. et al. . |
| 3,940,362 | 2/1976 | Overhults . |
| 3,961,966 | 6/1976 | Brinkmann et al. . |
| 3,995,641 | 12/1976 | Kronenthal et al. . |
| 4,035,334 | 7/1977 | Davydov et al. . |
| 4,125,494 | 11/1978 | Schoenberg et al. ................... 524/773 |
| 4,127,382 | 11/1978 | Perry . |
| 4,359,454 | 11/1982 | Hoffman ............................. 424/9.457 |
| 4,377,490 | 3/1983 | Shiraishi et al. ........................ 524/738 |
| 4,444,933 | 4/1984 | Columbus et al. . |
| 4,720,513 | 1/1988 | Kameyama et al. ..................... 523/203 |
| 4,980,086 | 12/1990 | Hiraiwa et al. .......................... 252/511 |
| 5,306,490 | 4/1994 | Barley, Jr. . |
| 5,328,687 | 7/1994 | Leung et al. . |
| 5,480,935 | 1/1996 | Greff et al. .............................. 524/776 |

OTHER PUBLICATIONS

James Quinn, M.D. and James Kissick, M.D., "Tissue Adhesives for Laceration Repair During Sporting Events", *Clinical Journal of Sport Medicine*, vol. 4, No. 4, 1994, pp, 245–248.

Capt. Stephen C. Woodard et al., "Histotoxicity of Cyanoacrylate Tissue Adhesive in the Rat*", *Annals of Surgery*, vol. 162, No. 1, Jul. 1965, pp. 113–121.

Yin–Chao Tseng et al., "In vivo Evaluation of 2–Cyanoacrylates as Surgical Adhesives", *Journal of Applied Biomaterials*, vol. 1, 1990, pp. 111–119.

Fred Leonard et al., "Synthesis and Degradation of Poly-(akyl α–Cyanoacrylates)", *Journal of Applied Polymer Science*, vol. 10, 1966, pp. 259–272.

*Primary Examiner*—Peter F. Kulkosky
*Attorney, Agent, or Firm*—Oliff & Berridge, PLC

[57] ABSTRACT

A biocompatible monomer composition includes: (A) at least one monomer, which forms a medically acceptable polymer; (B) at least one plasticizing agent present in the composition in an amount of from 0.5 wt. % to 15 wt. % of the composition; and (C) at least one acidic stabilizing agent having a $pK_a$ ionization constant of from about 1 to about 7. The composition can be applied to a variety of materials and is particularly suitable as in vivo tissue adhesive. A method of joining together in vivo two surfaces, e.g., body tissues, includes (a) holding damaged tissue edges together to form abutted tissue surfaces; (b) applying to the abutted tissue surfaces an excessive amount of a composition containing 1) at least one monomer, which forms a medically acceptable biodegradable polymer, 2) at least one plasticizing agent; and 3) at least one acidic stabilizing agent; and (c) maintaining the surfaces in contact until the composition polymerizes to form a thick film of polymerized composition bridging the abutted tissue surfaces.

19 Claims, No Drawings

MONOMERIC COMPOSITIONS EFFECTIVE AS WOUND CLOSURE DEVICES

FIELD OF THE INVENTION

This invention relates to monomer and polymer compositions useful to form biomedical adhesives and sealants, and methods of applying them. More particularly, this invention relates to wound closure monomer and polymer compositions and their use for medical, surgical and other in vivo applications.

BACKGROUND

Products in primary use for wound closure are surgical sutures and staples. Sutures are recognized to provide adequate wound support. However, sutures cause additional trauma to the wound site (by reason of the need for the needle and suture to pass through tissue and the need to anesthetize the wound area via needle application) and are time-consuming to place, and, at skin level, can cause unattractive wound closure marks. Surgical staples have been developed to speed wound apposition and provide improved cosmetic results. However, surgical staples also impose additional wound trauma and require the use of ancillary and often expensive devices for positioning and applying the staples. Both sutures and staples are especially problematic in pediatric cases where the patient may have a strong fear response and refuse to cooperate with their placement, and in geriatric cases where the skin tissue is weaker and prone to tearing.

Alternatively, adhesives have been proposed as wound closure devices. One group of such adhesives is the monomeric forms of alpha-cyanoacrylates.

Reference is made, for example, to U.S. Pat. No. 5,328,687 to Leung et al; U.S. Pat. No. 3,527,841 to Wicker et al.; U.S. Pat. No. 3,722,599 to Robertson et al.; U.S. Pat. No. 3,995,641 to Kronenthal et al.; and U.S. Pat. No. 3,940,362 to Overhults, which disclose alpha-cyanoacrylates that are useful as surgical adhesives. All of the foregoing references are hereby incorporated by reference herein.

Typically, the cyanoacrylate surgical adhesive is applied to one or both surfaces of wounds or incisions, including the internal portions of the wound, with any excess adhesive being quickly removed from the bonding surfaces. Subsequently, the edges of the wound are held together until they adhere. See U.S. Pat. No. 3,559,652 to Coover, Jr. et al. Two coatings of adhesive may be applied to the wound surfaces. However, this method of application produces significant levels of histoxicity due to the surgical adhesive being trapped within the wound site.

An additional method of application of the cyanoacrylate surgical adhesive to wounds or incisions involves the formation of a bridge over the wound site. As described in U.S. Pat. No. 3,667,472 to Halpern, the incised tissues are held together and maintained in fixed relationship until a cyanoacrylate adhesive has been applied over the incision and allowed the necessary time to develop a bond. Excess adhesive is removed from the incision. However, the composition utilized in this process suffers from inadequate film strength and flexibility with high histotoxicity in wound sites.

These conventional methods of application of tissue adhesive generally do not specify a particular method that is preferable, nor is there any mention of placing more than minimal amounts of glue upon wounds. The conventional application techniques strive to reduce application of excessive amounts of tissue adhesive to the wound due to histoxicity.

A topical tissue adhesive commercially available is Histoacryl® available from B. Braun Melsungen AG of Germany. The manufacturer recommends use of this adhesive only for closure of minor skin wounds and not for internal use. Moreover the manufacturer recommends that the adhesive be used sparingly or in thin films because thick films do not increase the film strength and can lead to necrosis of surrounding tissue due to thermogenic reaction. Moreover, films formed from this adhesive are brittle, permitting severe dehiscence of wounds.

Plasticizers have been added to cyanoacrylate surgical adhesive compositions. See, for example, U.S. Pat. No. 3,759,264 to Coover, Jr. et al., U.S. Pat. No. 3,667,472 to Halpern, U.S. Pat. No. 3,559,652 to Banitt, the subject matter of which is incorporated herein by reference. However, the incorporation of plasticizers in such compositions has led to decreased film strength of the polymerized material. Accordingly, such compositions have been utilized only within the wound site and not over the wound site as a bridge.

Other additives have been employed in cyanoacrylate surgical adhesives for the purposes of modifying the cure rate and shelf life of the adhesives. For example, cyanoacrylate polymerization inhibitors or stabilizers including Lewis acids, such as sulfur dioxide, nitric oxide, boron trifluoride and other acidic substances, including hydroquinone monomethyl ether, hydroquinone, nitrohydroquinone, catechol and hydroquinone monoethyl ether. See, for example, U.S. Pat. No. 3,559,652 to Banitt, the subject matter of which is incorporated herein by reference. These compositions contain significant amounts of impurities and, thus, require substantial amounts of stabilizer to inhibit premature polymerization of the monomer.

Other adhesives include both plasticizers and stabilizing agents. For example, U.S. Pat. No. 5,480,935 to Greff et al. describes a tissue adhesive having a plasticizer and a polymerization inhibitor. However, the plasticizers disclosed therein (i.e., alkyl phthalates) are highly toxic and are not suitable for use in biocompatible medical adhesives.

SUMMARY OF THE INVENTION

The present invention is based on the discovery that combining the monomers described hereinafter with a plasticizing agent and an acidic stabilizing agent provides a surgical adhesive composition that, after application to wounds or incisions, polymerizes to form a strong and flexible bond on the wound or incision site. Furthermore, the present invention provides a process for application of this surgical adhesive composition in a bridge structure that provides an unexpectedly improved bond strength over conventional application techniques of the polymerized composition on the wound or incision site, which increases the effectiveness of such monomers and polymers in in vivo applications.

The surgical adhesive forms a flexible and strong bond over wounds and incisions. Moreover, the method of applying a surgical adhesive to a wound or incision provides a strong and flexible biocompatible bond.

DETAILED DESCRIPTION OF PREFERRED EMBODIMENTS

One embodiment of the present invention provides a wound closure monomer composition, comprising:

A) at least one monomer, which forms a medically acceptable wound closure polymer:

B) at least one plasticizing agent; and

C) at least one acidic stabilizing agent.

In other embodiments, the present invention is directed to methods of using the above-described monomers, copolymers and polymers made therefrom for biomedical purposes.

In one such embodiment, the edges of a wound or incision are held together and an excessive amount of the above-described surgical adhesive composition is applied to the already pinched or abutted opposing wound edges, preferably utilizing more than one application stroke. This process forms a bridge over the abutted opposing wound edges that is flexible and possesses high tensile strength. The excessive amount of adhesive placed on the abutted opposing wound edges forms a thick film thereon and unexpectedly increases film strength.

For example, the present invention includes a method of forming a biocompatible film across abutted tissue surfaces, comprising; (a) holding together at least two tissue surfaces to form abutted tissue surfaces, (b) applying across said abutted tissue surfaces an adhesive biocompatible monomer composition, and (c) allowing said composition to polymerize and form a biocompatible film on said abutted tissue surfaces having an in vivo film strength of at least 70 mmHg of vacuum pressure required to induce wound failure, generally from 70 mmHg to 400 mmHg of vacuum pressure required to induce wound failure, preferably from 90 mmHg to 400 mmHg of vacuum pressure required to induce wound failure, and more preferably from 100 mmHg to 400 mmHg of pressure required to induce wound failure.

Preferably, the monomer is an alpha-cyanoacrylate. The monomer compositions of this invention and polymers formed therefrom are useful as tissue adhesives, sealants for preventing bleeding or for covering open wounds, and in other biomedical applications. They find uses in, for example, apposing surgically incised or traumatically lacerated tissues; setting fractured bone structures; retarding blood flow from wounds; and aiding repair and regrowth of living tissue.

As above-mentioned, conventional surgical adhesive compositions have included plasticizers with the adverse effect of reducing the film strength. It has been discovered that, contrary to prior belief, the film strength (e.g., toughness) under certain conditions is not adversely reduced upon the addition of greater amounts of plasticizing agent. Depending on the particular acidic stabilizing agent and the purity of the monomer utilized in the adhesive composition, the addition of greater amounts of plasticizing agent may increase the toughness of the resulting bond formed on the wound. It has been discovered that weak acidic stabilizing agents do not significantly affect the polymerization of the monomer in the present composition and provide increased film strength with increasing amounts of plasticizing agents.

Monomers that may be used in this invention are polymerizable, e.g. anionically polymerizable or free radical polymerizable, to form polymers. Such monomers include those that form polymers, which may, but do not need to, biodegrade. Reference is made, for example, to U.S. Pat. No. 5,328,687, which is hereby incorporated by reference herein. As defined herein, "histotoxicity" refers to adverse tissue response, such as inflammation due to the presence of toxic materials in the tissue.

Useful 1,1-disubstituted ethylene monomers include, but are not limited to, monomers of the formula:

$$CHR=CXY \qquad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include alpha-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula

(II)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula

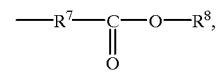

wherein R$^7$ is

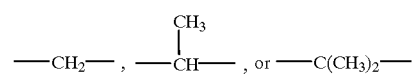

and R$^8$ is an organic radical.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic radical R$^8$ may be substituted or unsubstituted and may be straight chain, branched or cyclic, saturated, unsaturated or aromatic. Examples of such organic radicals include C$_1$–C$_8$ alkyl radicals, C$_2$–C$_8$ alkenyl radicals, C$_2$–C$_8$ alkynyl radicals, C$_3$–C$_{12}$ cycloaliphatic radicals, aryl radicals such as phenyl and substituted phenyl and aralkyl radicals such as benzyl, methylbenzyl and phenylethyl. Other organic radicals include substituted hydrocarbon radicals, such as halo(e.g., chloro-, fluoro- and bromo-substituted hydrocarbons) and oxy-(e.g., alkoxy substituted hydrocarbons) substituted hydrocarbon radicals. Preferred organic radicals are alkyl, alkenyl and alkynyl radicals having from 1 to about 8 carbon atoms, and halo-substituted derivatives thereof. Particularly preferred are alkyl radicals of 4 to 6 carbon atoms.

In the cyanoacrylate monomer of formula (II), R$^3$ is preferably an alkyl group having 1–10 carbon atoms or a group having the formula —AOR$^9$, wherein A is a divalent straight or branched chain alkylene or oxyalkylene radical having 2–8 carbon atoms, and R$^9$ is a straight or branched alkyl radical having 1–8 carbon atoms.

Examples of groups represented by the formula —AOR$^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

The alpha-cyanoacrylates of formula (II) can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein $R^3$ is a group having the formula $—R^4—O—R^5—O—R^6$ can be prepared according to the method disclosed in U.S. Pat. No. 4,364,876 to Kimura et al., which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or paraformaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (II) wherein $R^3$ is a group having the formula

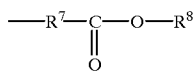

can be prepared according to the procedure described in U.S. Pat. No. 3,995,641 to Kronenthal et al., which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

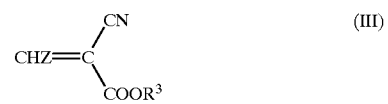

wherein Z is $—CH=CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated by reference herein.

Preferred monomers are alkyl alpha-cyanoacrylates and more preferably octyl alpha-cyanoacrylates, especially 2-octyl alpha-cyanoacrylate. Monomers utilized in the present application should be very pure and contain few impurities (e.g., surgical grade).

Component B) of the compositions of this invention is at least one plasticizing agent that imparts flexibility to the polymerized monomer formed on the wound or incision. The plasticizing agent preferably contains little or no moisture and should not significantly affect the polymerization of the monomer.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate and mixtures thereof. Preferred plasticizers are tributyl citrate and acetyl tributyl citrate.

Component C) of the compositions of this invention is at least one acidic stabilizing agent that inhibits polymerization. Such stabilizing agents may also include mixtures of anionic stabilizing agents and radical stabilizing agents.

Examples of suitable anionic stabilizing agents include sulfur dioxide, sulfonic acid, lactone, boron trifluoride, organic acids, alkyl sulfate, alkyl sulfite, 3-sulfolene, alkylsulfone, alkyl sulfoxide, mercaptan, and alkyl sulfide and mixtures thereof. Preferable anionic stabilizing agents are acidic stabilizing agents of organic acids such as acetic acid or phosphoric acid with acetic acid being a more preferable acidic stabilizing agent. The maximum amount of sulfur dioxide present in the adhesive composition should be less than 50 ppm, and preferably less than 30 ppm.

Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, and t-butyl hydroquinone.

Suitable acidic stabilizing agents include those having $pK_a$ ionization constants ranging from about 0 to about 7, preferably from about 1 to about 6, and more preferably from about 2 to about 5.5. For example, suitable acidic stabilizing agents include: hydrogen sulfide ($pK_a$ 7.0), carbonic acid ($pK_a$ 6.4), triacetylmethane ($pK_a$ 5.9), acetic acid ($pK_a$ 4.8), benzoic acid ($pK_a$ 4.2), 2,4-dinitrophenol ($pK_a$ 4.0), formic acid ($pK_a$ 3.7), nitrous acid ($pK_a$ 3.3), hydrofluoric acid ($pK_a$ 3.2), chloroacetic acid ($pK_a$ 2.9), phosphoric acid ($pK_a$ 2.2), dichloroacetic acid ($pK_a$ 1.3), trichloroacetic acid ($pK_a$ 0.7), 2,4,6-trinitrophenol (picric acid) ($pK_a$ 0.3) trifluoroacetic acid ($pK_a$ 0.2), and mixtures thereof.

When adding the above-mentioned weak acidic stabilizing agents to the adhesive composition, it has been discovered that the addition of plasticizing agents in amounts ranging from about 0.5 wt. % to about 16 wt. %, preferably from about 3 wt. % to about 9 wt. %, and more preferably from about 5 wt. % to about 7 wt. % provides increased film strength (e.g., toughness) of the polymerized monomer over polymerized monomers having amounts of plasticizing agents and acidic stabilizing agents outside of the above ranges.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid, such as phosphoric acid a concentration range of 20–80 ppm (wt/wt), preferably, 30–70 ppm (wt/wt) and more preferably 40–60 ppm (wt/wt) may be utilized.

The compositions of this invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a β-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soybean protein, vegetable protein, keratin and glue. The preferred protein for use in this invention is casein.

Suitable amides for use in this invention include urea, cyanamide, acrylamide, benzamide, and acetamide. Urea is the preferred amide.

Suitable alcohols include phenols, 1,4-butanediol, d-sorbitol, and polyvinyl alcohol.

Examples of suitable compounds having a β-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated by reference herein. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In practicing this invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved, by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such "bioerosion" can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, copolymers of polyglycolic acid and polylactic acid, polycaprolactone, poly-β-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly (anhydrides); poly(alkyl-2-cyanoacrylates); poly (dihydropyrans); poly(acetals); poly(phosphazenes); poly (urethanes); poly(dioxinones); cellulose; and starches.

Examples of the surfactant which can be added to the mineral oil include those commercially available under the designations Triton x-100, Tween 20 and Tween 80.

The composition of this invention may further contain one or more adjuvant substances, such as thickening agents, medicaments, or the like, to improve the medical utility of the monomer for particular medical applications.

Suitable thickeners include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

To improve the cohesive strength of adhesives formed from the compositions of this invention, difunctional monomeric cross-linking agents may be added to the monomer compositions of this invention. Such crosslinking agents are known. Reference is made, for example, to U.S. Pat. No. 3,940,362 to Overhults, which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator is added to initiate polymerization of the cyanoacrylate monomer/crosslinking agent blend.

The compositions of this invention may further contain fibrous reinforcement and colorants, i.e., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl) axo]-2-naphthalene-sulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phtha-1-ocyaninato (2-)] copper.

The compositions of this invention can be used to join together two surfaces by applying the present composition to the surface of opposing wound surfaces that are held together. Depending on the particular requirements of the user, the adhesive compositions of this invention can be applied by known means such as with a glass stirring rod, sterile brush or medicine dropper. However, in many situations a pressurized aerosol dispensing package is preferred in which the adhesive composition is in solution with a compatible anhydrous propellant.

In one embodiment, the present invention is directed to a method of joining together in vivo two surfaces which comprises (a) holding together tissue surfaces of a wound or incision to form an abutted tissue surface; (b) applying to said abutted tissue surface a composition of the present invention, e.g., a composition comprising 1) at least one monomer (e.g., a monomer of formula (I)) which forms a medically acceptable polymer, 2) a plasticizing agent and 3) a suitable acidic stabilizing agent; and (b) maintaining the surfaces in contact until said composition polymerizes.

As above-mentioned, conventional surgical adhesive compositions have been applied in very small quantities to wound surfaces before they are abutted, with care taken to remove excess adhesive. Thick films formed on wound surfaces have, in the past, resulted in increased histotoxicity of the wound tissues and increased film brittleness with no increased film strength.

However, the present invention is directed to a method of joining together in vivo two tissue surfaces by applying to an already abutted tissue surface of a wound or incision a composition of this invention, preferably in more than one application or coating on the abutted tissue surfaces to provide an excess of the adhesive composition on the abutted tissue surfaces. Any excess adhesive applied directly on the abutted tissue surface or on the immediate vicinity of the wound or incision is preferably not removed, although excess applied to surrounding tissue not proximate to the wound region may be removed.

A subsequent coating may be applied immediately after application of a previous coating or after a previous coating has been completely polymerized. Preferably, the monomer composition applied to the abutted tissue surface is allowed to at least partially polymerize prior to subsequent coatings or applications of additional monomer composition. A coating of an adhesive composition of the present invention having a monomer different from the monomer of the first or previous coating may be applied as the second or subsequent coating. Due to the addition of the plasticizing agent and the acidic stabilizing agent, the polymer formed on the abutted tissue surface possesses sufficient bond strength and flexibility even with significant film or coating thicknesses. Suitable film thickness range from 0.1 mm to 2.0 mm or 3.0 mm or higher, preferably from 0.2 mm to 1.5 mm and more preferably from 0.4 mm to 0.8 mm.

In another embodiment, the present invention is directed to a method of joining together in vivo two tissue surfaces by application of the present adhesive composition utilizing various applicators. Such applicators include crushable swab applicators, syringes and vials with various dispensing nozzles or tips.

For example, the applicator tip may be detachable from the applicator container holding the polymerizable and/or cross-linkable material. Such an applicator tip could be attached to the applicator container prior to use and detached from the applicator container subsequent to use in order to prevent premature polymerization or cross-linking of the unapplied material in the applicator container. At this point the applicator tip may be discarded and a new applicator tip may be attached to the applicator container for subsequent use or the applicator tip may be reused.

Additionally, the applicator tip according to the present invention may comprise multiple parts, with at least one part comprising the initiator. For example, the component comprising the initiator may be fabricated separately from the other component(s) of the applicator tip and assembled prior to attachment to the applicator container.

The applicator tip may also be in the form of a nozzle for atomizing liquid polymerizable and/or cross-linkable materials. Conical, flat spray or condensed stream nozzles are suitable.

The applicator tip according to the present invention may be utilized in various devices. For example, manual methods of application may include utilization of hand-held devices such as syringes, adhesive guns, pipettes, eyedroppers and the like.

The applicator tip and the applicator container may also be an integral unit. The unit may be preformed as a single piece and charged with polymerizable and/or cross-linkable material. After application of material from the applicator container, the unit may be discarded. Additionally, such an integral applicator tip/applicator container unit may be fashioned to provide the capability of recharging the unit with new material as a multiple use device.

The applicator tip may be composed of any of a variety of materials including polymerized materials such as plastics, foams, rubber, thermosets, films or membranes. Additionally, the applicator tip may be composed of materials such as metal, glass, paper, ceramics, cardboard and the like. The applicator tip material may be porous, absorbent or adsorbent in nature to enhance and facilitate loading of the initiator on or within the applicator tip. For example, the applicator tip may be composed of a material having random pores, a honey-comb material, a material having a woven pattern, etc. The degree of porosity will depend on the materials being used.

The applicator tip according to the present invention, where it connects to the applicator container, may have an elongated tubular portion, out of which the mixed polymerizing and/or cross-linking material is expelled. A portion of the applicator tip which is immediately downstream of the applicator container is advantageously porous in order to avoid a sharp pressure drop and ensure a constant mixed ratio profile. The structure can preferably trap any barriers or materials used to separate multiple components within the applicator container. Thus, any such barriers will not clog the device.

Initiators that initiate polymerization and/or cross-linking of the material may be applied to a surface portion or to the entire surface of the applicator tip, including the interior and the exterior of the tip. Alternatively, the initiator may be coated only on an internal surface of the applicator tip. Preferably, only a portion of the interior of the applicator tip is coated with the initiator.

The initiator on the applicator tip may be in the form of a solid, such as a powder or a solid film, or in the form of a liquid, such as a viscous or paste-like material. The initiator may also include a variety of additives, such as surfactants or emulsifiers. Preferably, the initiator is soluble in the polymerizable and/or cross-linkable material, and/or comprises or is accompanied by at least one surfactant which, in embodiments, helps the initiator co-elute with the polymerizable and/or cross-linkable material. In embodiments, the surfactant may help solubilize the initiator in the polymerizable and/or cross-linkable material.

Particular initiators for particular systems may be readily selected by one of ordinary skill in the art without undue experimentation. Suitable initiators include, but are not limited to, detergent compositions; surfactants: e.g., non-ionic surfactants such as polysorbate 20 (e.g., Tween 20™), polysorbate 80 (e.g., Tween 80™) and poloxamers, cationic surfactants such as benzalkonium chloride and tetrabutylammonium bromide, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators and radicals, such as di-t-butyl peroxide and azo-bisisobutyronitrile. The polymerizable and/or cross-linkable material may also contain an initiator which is inactive until activated by a catalyst or accelerator (included within the scope of the term "initiator" as used herein) in the applicator tip. Initiators activated by stimulation such as heat and/or light (e.g., ultraviolet or visible light) are also suitable if the tip and/or applicator is appropriately subjected to such stimulation.

The initiator may be applied to the surface of the applicator tip or may be impregnated or incorporated into the matrix or internal portions of the applicator tip. For example, the initiator may be applied to the applicator tip by spraying, dipping, or brushing the applicator tip with a liquid medium containing the initiator. The liquid medium may include non-aqueous solvents, such as ether, acetone, ethanol, pentane or mixtures thereof; or may include aqueous solutions. Preferably, the liquid medium is a low boiling point solvent.

Suitable applicators for application of the adhesive of the present invention include those described in copending application Ser. No. 08/488,411, the subject matter of which is incorporated herein by reference. A preferable applicator is a crushable swab applicator.

Specific methods which may use an adhesive composition of the present invention include methods for repairing damaged living tissue to prevent the escape of fluids therethrough by holding damaged tissue edges together in an abutting relationship, applying to the abutting tissue the monomer composition of the present invention, and allowing the composition to polymerize; methods for stemming the flow of blood from vessels which comprises holding damaged regions of the blood vessels together, applying the present monomer composition to the damaged regions and allowing the composition to polymerize; and methods of bonding bone tissue to promote healing of weak or fractured bones which comprises holding damaged bone tissue together, applying to the damaged tissue the present monomer composition, and allowing the composition to polymerize.

Repairing injured tissues (for example, to control bleeding) comprises, in general, sponging to remove superficial body fluids, holding injured tissue surfaces together in an abutting relationship and subsequent application to the exposed abutted tissue of the present adhesive composition. The composition polymerizes to a thin film of polymer while in contact with the abutted tissue surface. Tissues which are not bleeding or otherwise covered by body fluids need not be sponged first. More than one coating or application of monomer composition may be applied to the abutted tissue surface.

The monomers are readily polymerized to addition-type polymers and copolymers, which are generally optically clear (as films).

In most bonding applications using the compositions of this invention, polymerization of the monomers is catalyzed by small amounts of moisture on the surface of the adherents; thus desired bonding of tissues or hemostasis proceeds well in the presence of blood and other body fluids. The bonds formed are of adequate flexibility and strength to withstand normal movement of tissue. In addition, bond strength is maintained as natural wound healing proceeds.

Compositions employed in the invention are preferably sterilizable by conventional methods that include, but are not limited to, autoclave or aseptic filtration techniques.

EXAMPLES I–VI

The compositions according to the present invention are prepared utilizing conventional mixing equipment. For example, the process may be conducted as follows:

To a surgical grade cyanoacrylate in a round-bottom flask is added the plasticizer, the acidic stabilizer, and other formulation components as described herein. The resulting mixture is mechanically stirred until it is homogeneous.

The invention is further illustrated by the following non-limiting examples.

In the following examples, various amounts of plasticizer (i.e., acetyl tributyl citrate) are utilized in adhesive compositions of the present invention that illustrate the effects on the strengths of the bonds formed by the adhesive.

The data presented in Table I is generated using the following method:

1. A 2" incision is made in a 5½"×5½" sheet of latex (1/16" thickness).
2. An adhesive composition (i.e., 2-octyl cyanoacrylate) is applied topically to the incision with a crushable swab with a polymerization initiated tip. The interface of the incision must not be inadvertently glued.
3. After curing for one hour, the sheet is fixed between two sheets of plexiglass. The bottom sheet is equipped with a pressure transducer and gas inlet. The upper sheet has a 3⅝" hole centrally located in it. The test piece is positioned such that the glued side is facing the upper sheet of plexiglass containing the 3⅝" hole.
4. The valve controlling gas flow is opened to pressurize the test material. Pressure is increased until failure.
5. Peak pressure is recorded by the transducer and recorded on a chart recorder. Ten determinations per test material are made.

The results are as follows:

TABLE I

| EXAMPLE | Concentration (w/w %) of Plasticizer | BURST PRESSURE (psi) |
| --- | --- | --- |
| I | 0.0 | 3.9 |
| II | 5.7 | 3.9 |
| III | 9.1 | 3.7 |
| IV | 15.2 | 3.2 |
| V | 20.0 | 2.6 |
| VI | 25.9 | 2.1 |

EXAMPLES VII–X

In order to demonstrate the unexpected superiority of the in vivo film strength provided by the adhesive composition and application method according to the present invention, various methods and materials for wound closure and topical administration of various surgical wound closure devices are evaluated (Examples VII–X). In vivo strength is objectively defined by the amount of ultimate pressure required to induce wound failure (i.e., the amounts of vacuum pressure required to open the wound). The biomechanical analysis is performed using the Dimensional Analysis Systems (DAS), (DIMENSIONAL ANALYSIS SYSTEMS, LEONIA, N.J.). This technology is specifically designed for objective in vivo biomechanical characterization of linear incision wounds. In contrast to previous biomechanical analysis methods (e.g., uniaxial tensiometers), the DAS applies a multi-axial stress to a wound which is more analogous to stresses experienced in clinical conditions. Moreover, the DAS does not require tissue manipulation or destructive incision of specimens prior to testing. Therefore, sensitive, reliable and reproducible measurements of fragile wounds may be obtained in the early phases of healing. The DAS further eliminates the artifact error and the experimental variables introduced by excisional methods such as, non-viable tissue samples, inconsistent variation of sample dimensions, and flawed edges from excising tissues.

The male Sprague Dawley rat is selected for the animal model because of its genetic homogeneity, ease of handling and housing, and overall popularity as a linear incision wound model, thus allowing comparison of data to other similar studies. This model has been used extensively in incisional wound research, which is well documented in the literature.

Male Sprague Dawley rats, purchased from Harlan Sprague Dawley, Inc. (Indianapolis, Ind.) are utilized in the tests. All animals are held seven days prior to the procedures for stabilization of diet and behavior. Four groups of rats (Groups A–D), each with a different wound closure method and/or surgical adhesive, are tested under identical conditions. Each of the specimens are tested for film strength one hour after closure of the linear incision wounds.

EXAMPLE VII

In the first group of rats, designated as Group A, a one-stroke technique for application of tissue adhesive is employed. An adhesive of the present invention containing about 6% by weight of plasticizer with acetic acid as an acidic stabilizer ($pK_a$=4.8) in 2-octyl alpha-cyanoacrylate is applied with a compressible ampule with a swab tip (crushable swab applicator) and is passed along the opposing wound edges in a "one-stroke" fashion for topical administration.

EXAMPLE VIII

In the second group of rats, designated as Group B, linear incisions are closed with the same adhesive using a multi-stroke technique. The adhesive is applied with a compressible ampule passed more than once along the opposing wound edges in a "multi-stroke" fashion, resulting in 2–3 distinct applications of adhesive.

EXAMPLE IX

In the third group of rats, designated as Group C, linear incision wounds are closed with the same adhesive using a minimal surface exposure technique. Adhesive is applied with a UniJect™ syringe (available from Horizon, Santa Ana, Calif., USA) with approximately 3–4 drops in an attempt to limit the amount of adhesive exposed to the skin surface, thus administering the adhesive to the opposing wound edges only.

EXAMPLE X

In the fourth group of rats, designed as Group D, linear incision wounds are closed with Histoacryl™ (a surgical adhesive available from B. Braun Melsungen AG of Germany) using the application technique of Example IX.

The results from the in vivo biomechanical analyses are displayed in Table II below. As illustrated in Table II, there are significant differences observed between all groups at the one hour time period studied. Group B, the multi-stroke technique, demonstrates a significant increase in ultimate pressure in comparison to Groups A & C. This data suggests that increasing the amount of adhesive applied may allow for higher in vivo strength. Group D reveals a highly significant decrease in in vivo strength in comparison to all groups evaluated.

TABLE II

Reveals statistical results for direct comparisons of the alternate methods and other techniques at 1 hour post-application

| Group | Number of Incisions | In Vivo strength (mmHg) |
| --- | --- | --- |
| A: one stroke | 10 | 110.30 |
| B: multi-stroke | 10 | 214.57 |
| C: minimal surface exposure | 10 | 94.36 |

TABLE II-continued

Reveals statistical results for direct comparisons of the alternate methods and other techniques at 1 hour post-application

| Group | Number of Incisions | In Vivo strength (mmHg) |
| --- | --- | --- |
| D: Histoacryl (minimal surface exposure) | 10 | 62.80 |

EXAMPLE XI

The efficacy of the same tissue adhesive according to the present invention is tested in its ability to close skin incisions in a pig model. The tissue adhesive, Histoacryl™, is used as a control.

Incisions are made on each side of the back of these pigs with sterile scalpel blades at a controlled depth for the incisions. The incisions are closed either with the test material or with the control. The same adhesive of the present invention, incorporated into an applicator, was applied onto the opposed abutted edges of the wound until the adhesive polymerizes (i.e., the adhesive is no longer sticky to the touch). The applicator is a transparent, flexible, plastic cylinder with an absorbent head (crushable swab). Within the cylinder is a glass vial containing the adhesive which is broken by squeezing the cylinder. As the applicator is inverted, the adhesive is squeezed out of the cylinder into the head and then onto the skin. Histoacryl® is also applied with an applicator, which is a sealed plastic ampule with a narrow neck. The ampule is attached to a 27 gauge hypodermic needle. The ampule is inverted and the adhesive is applied by squeezing the ampule and dripping microdrops from the end of the needle onto the opposed edges of the incision. Care is taken not to touch the skin with the needle tip. The method of applying Histoacryl® has been described by J. Quinn and J. Kissick (1994, "Tissue adhesives for laceration repair during sporting events", *Clin. J. Sport Med.*, 4:245–248).

Observations are made frequently during the recovery phase, recorded approximately four hours postoperatively, and then daily to determine if any of the incisions partially or completely separates (dehiscence), and if there are any adverse tissue responses. If a wound opens during the observation period, it is not reclosed.

TABLE III

DEHISCENCE OF PIG SKIN INCISIONS

|  | Invention ™ | Histoacryl ™ |
| --- | --- | --- |
| PIG 1 | | |
| Number of incisions | 4 | 4 |
| Number of partial or complete dehiscences | 0 | 1 |
| PIG 2 | | |
| Number of incisions | 4 | 4 |
| Number of partial or complete dehiscences | 0 | 4 |
| PIG 3 | | |
| Number of incisions | 4 | 4 |
| Number of partial or complete dehiscences | 0 | 2 |

The pigs are observed for wound dehiscence for 10 days. Dehiscence is not observed in any incision closed with the adhesive of the invention. Partial or complete dehiscence is observed in 7 of the 12 incisions closed with Histoacryl™. Complications such as infection or necrosis are not observed.

What is claimed is:

1. A biocompatible monomer composition, comprising:
   A. at least one monomer, which forms a medically acceptable polymer;
   B. at least one plasticizing agent present in the composition in an amount of from 0.5 wt. % to 16 wt. % of the composition;
   C. at least one acidic stabilizing agent having a $pK_a$ ionization constant of from about 0 to about 7; and
   D. an initiator selected from the group consisting of surfactants, imidazole, tryptamine, urea, arginine, povidine, phosphines, triethyl phosphite, phosphonium salts, methyl gallate, ascorbic acid, tannic acid, sodium bisulfite, magnesium hydroxide, calcium sulfate, sodium silicate, thiourea, polysulfides, monensin, nonactin, calixarenes, polymeric epoxides, carbonates, cobalt napthenate, manganese acetylacetonate and phase transfer catalysts.

2. A composition according to claim 1, wherein said at least one plasticizing agent is present in an amount of from 3 wt. % to 9 wt. % of said composition.

3. A composition according to claim 1, wherein said at least one plasticizing agent is present in an amount of from 4 wt. % to 7 wt. % of said composition.

4. A composition according to claim 1, wherein said at least one acidic stabilizing agent has a $pK_a$ of from about 1 to about 7.

5. A composition according to claim 1, wherein said at least one plasticizing agent is present in an amount ranging from 3 wt. % to 9 wt. % of said composition and said at least one acidic stabilizing agent has a $pK_a$ of from about 1 to about 6.

6. A composition according to claim 1, wherein said at least one plasticizing agent is present in an amount of 5 wt % to 7 wt % of said composition and said at least one acidic stabilizing agent has a $pK_a$ of about 2 to about 5.5.

7. A composition according to claim 1, wherein said plasticizing agent is selected from the group consisting of acetyl tributyl citrate, tributyl citrate and mixtures thereof.

8. A composition according to claim 1, wherein said acidic stabilizer is acetic acid.

9. A composition according to claim 1, wherein said monomer is 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

10. A composition according to claim 1, wherein said composition comprises at least two different monomers.

11. The biocompatible composition according to claim 1, wherein said plasticizing agent is selected from the group consisting of dimethyl sebacate, triethyl phosphate, tri(2-ethylhexyl)phosphate, glyceryl triacetate, glyceryl tributyrate, diethyl sebacate, dioctyl adipate, isopropyl myristate, butyl stearate, lauric acid, trioctyl trimellitate, dioctyl glutarate and tributyl citrate.

12. The biocompatible monomer composition according to claim 1, wherein said initiator is inactive until activated by a stimulant selected from the group consisting of a catalyst, an accelerator, heat and light.

13. The biocompatible monomer composition according to claim 1, wherein said surfactants are selected from the group consisting of polysorbate 20, polysorbate 80, poloxamers, benzalkonium chloride, tetrabutylammonium bromide, sodium tetradecyl sulfate and dodecyldimethyl(3-sulfopropyl)ammonium hydroxide.

14. The biocompatible monomer composition according to claim 1, further comprising a formaldehyde scavenger.

15. The biocompatible monomer composition according to claim 14, wherein said formaldehyde scavenger is selected from the group consisting of sulfites, bisulfites, ammonium sulfite salts, amines, amides, imides, nitrites, carbamates, alcohols, mercaptans, proteins, active methylene compounds, heterocyclic ring compounds free of a carbonyl group and containing an NH group, and combinations thereof.

16. The biocompatible monomer composition of claim 1, wherein said at least one acidic stabilizing agent having a $pK_a$ ionization constant of from about 0 to about 2.

17. The biocompatible monomer composition according to claim 1, wherein said stabilizing agent further comprises an anionic or radical stabilizing agent selected from the group consisting of alkyl sulfate, alkyl sulfite, mercaptan, alkyl sulfide, benzoquinone, 2-hydroxybenzoquinone, p-methoxy phenol, butylated hydroxy anisole, butylated hydroxy toluene and mixtures thereof.

18. The biocompatible monomer composition according to claim 16, wherein said stabilizing agent is present in an amount of 20–200 ppm.

19. The biocompatible monomer composition according to claim 1, wherein said stabilizing agent is sulfur dioxide and is present in an amount less than 30 ppm.

* * * * *